United States Patent [19]

Sisto et al.

[11] Patent Number: 5,760,248
[45] Date of Patent: Jun. 2, 1998

[54] TACHYKININ ANTAGONISTS

[75] Inventors: Alessandro Sisto, Rome; Christopher Fincham, Pomezia; Edoardo Potier, Rome; Stefano Manzini, Florence; Federico Arcamone, Nerviano; Paolo Lombardi, Cesate, all of Italy

[73] Assignee: A.Menarini Industrie Farmaceutiche Riunite S.r.l., Florence, Italy

[21] Appl. No.: 656,068

[22] Filed: May 31, 1996

Related U.S. Application Data

[63] Continuation-in-part of PCT/EP94/04012, Dec. 2, 1994, published as WO95/15311 Jun. 8, 1995.

[30] Foreign Application Priority Data

Dec. 3, 1993 [IT] Italy .................. FI93A0247

[51] Int. Cl.$^6$ .................. C07D 209/02; C07D 209/42; A61K 31/40
[52] U.S. Cl. .................. 548/492; 514/415; 514/418; 514/419; 548/483; 548/484; 548/485; 548/486; 548/495
[58] Field of Search .................. 514/415, 418, 514/419; 548/483, 484, 485, 486, 492, 495

[56] References Cited

U.S. PATENT DOCUMENTS 5,641,802  6/1997  Arcamone et al. .................. 514/419

FOREIGN PATENT DOCUMENTS 0333174  of 1989  European Pat. Off.
9118899  of 1991  WIPO.
9413694  of 1994  WIPO.

OTHER PUBLICATIONS

Hagiwara et al., J. Med. Chem., 36, 2266–2278 (1993).
Mantyh et al., Proc. Natl. Acad. Sci. USA, 85, 3235 (1988).
STN search report for: Potier et al., New NK-1 Tachykinin Receptor Antagonists Based on a Alicyclic Amino Acids as a Template: Stereoselective Synthesis and Chirality Investigation by NMR, Pept. 1994, Proc. Eur. Symp., 23rd, Meeting Date 1994, p. 315–, 1995.
Sisto et al., Synthesis and Biological Evaluation of Novel NK-1 Tachykinin Receptor Antagonists: The Use of Cycloalkyl Amino Acids as a Template, Biopolymers, vol. 36, No. 4, pp. 511–524, Oct. 1995.
Peters et al., Amer. Rev. Resp. Dis. 145,835 (1992).
Regoli et al., Pharmacology, 28, 301–320 (1984).
Hamel et al., Can. J. Pharm. Physiol., 66, 1361 (1988).

*Primary Examiner*—Mukund J. Shah
*Assistant Examiner*—Brenda Coleman
*Attorney, Agent, or Firm*—Abelman, Frayne & Schwab

[57] ABSTRACT

A description is given of tachykinin receptor antagonists having general formula (I)

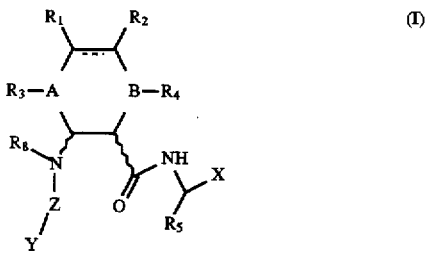

their preparation and use in pharmaceutical formulations.

7 Claims, No Drawings

TACHYKININ ANTAGONISTS

This application is a continuation-in-part of International Application PCT/EP94/04012 having an international filing date of Dec. 2, 1994, published as WO95/15311 Jun. 8, 1995.

FIELD OF THE INVENTION

The present invention refers to tachykinin antagonists, their preparation and use in pharmaceutical formulations.

In particular, the present invention refers to compounds having general formula (I)

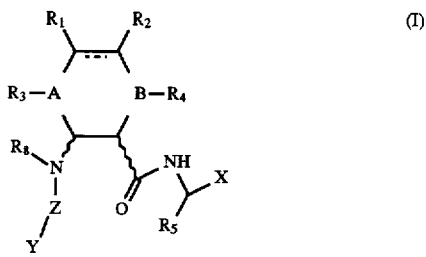

wherein:

Y is selected out of a group consisting of an aryl-, aryl-alkyl- radical containing 7 to 12 carbon atoms wherein the aryl moiety is selected out of the group consisting of pyridine, benzene, naphthyl, tetrahydroquinoline, imidazole and wherein the aromatic ring is unsubstituted or substituted with one or more substituent(s) selected from a group consisting of halogen, a linear or branched alkyl radical containing 1 to 6 carbon atoms, possibly substituted with not more than three fluorine atoms, a linear or branched oxyalkyl radical containing not more than three fluorine atoms, —NH2, —NHR11, —N(R11)2, —CONHR11, —COR11, —COOR11, —R12COOR11, —CONHR11, —R12CONHR11, —NHCOR11, —NHCCOOR11, —R12COOR11, nitro, wherein R11 and R12 are independently selected from H, a linear or branched alkyl radical containing 1 to 6 carbon atoms; a radical of type

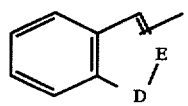

wherein D stands for O, S, CH2, N-R9 where R9 is selected from a group consisting of H, a linear or branched alkyl radical containing 1 to 6 carbon atoms, acyl radical R10-CO wherein R10 is selected from H, a linear or branched alkyl radical containing 1 to 3 carbon atoms and E=CH or N, each with suitable substituents;

Z is selected from the group consisting of CH2 and CO;

R8 is selected from a group consisting of H, a linear or branched alkyl radical containing 1 to 6 carbon atoms;

symbol ∼∼∼ represents a single or a double bond: if the bond is single, R1 and R2 are selected out of a group consisting of hydrogen, hydroxyl, methoxy-ethoxy-ethoxyl or methoxy-ethoxy-methoxyl, and halogen or are joined to form an epoxide; if the bond is double, they are hydrogen or halogen; A and B stand for CH; R3 and R4 are selected out of the group consisting of hydrogen, a linear or branched alkyl radical containing 1 to 6 carbon atoms, or are joined together to form a —(CH2)n- bridge, where n stands for a whole number from 1 to 3;

R5 is selected out of a group consisting of an aryl-, aryl-alkyl-, alkyl-aryl- radical containing up to 15 carbon atoms, wherein the aryl-moiety is selected out of the group consisting of pyridine, benzene, naphthyl, tetrahydroquinoline, imidazole, indole, benzofurane and wherein the aromatic ring is unsubstituted or substituted with one or more substituent(s) selected from a group consisting of halogen, a linear or branched alkyl radical containing 1 to 6 carbon atoms, possibly substituted with not more than three fluorine atoms, a linear or branched oxyalkyl radical containing not more than three fluorine atoms, —NH2, —NHR11, —N(R11)2, —CONHR11, —COR11, —COOR11, —R12COOR11, —CONHR11, —R12CONHR11, —NHCOR11, —NHCOOR11, —R12COOR11, nitro, wherein R11 and R12 are as defined above;

X is selected from a group consisting of COOR6, —CH2OR6, —NR7COR6, —NR6COOR7, —CONR6R7, R6 and R7 are independently selected out of a group consisting of H, alkyl, aryl-, aryl-alkyl- radical containing up to 15 carbon atoms wherein the aryl moiety is selected out of the group consisting of pyridine, benzene, naphthyl, tetrahydroquinoline, imidazole, indole, benzofurane and wherein the aromatic ring is unsubstituted or substituted with one or more substituent(s) selected from a group consisting of halogen, a linear or branched alkyl radical containing 1 to 6 carbon atoms, possibly substituted with not more than three fluorine atoms, a linear or branched oxyalkyl radical containing not more than three fluorine atoms, —NH2, —NHR11, —N(R11)2, —CONHR11, —COR11, —COOR11, —R12COOR11, —CONHR11, —R12CONHR11, —NHCOR11, —NHCOOR11, —R12COOR11, nitro, wherein R11 and R12 are as defined above, with the proviso that if X=—CONR6R7 then Z is other than CO or R8 is other than H.

Symbol ∼∼∼ means that the configuration of those asymmetric carbon atoms of 2-amino-cyclohexanecarboxylic acid could be either S or R, with the proviso that such configuration can not be S or R for both the asymmetric carbon atoms (the two substituents must be cis).

Tachykinin antagonist compounds as per formula (I) prove to be effective in the treatment of diseases where tachykinins play a pathogenic role, in particular in the treatment of arthritis, asthma, inflammations, tumoral growth, gastrointestinal hypermotility, Huntington's disease, neuritis, neuralgia, migraine, hypertension, incontinence of urine, urticaria, carcinoid syndrome symptoms, influenza, and cold, disorders related to immune system.

STATE OF THE ART

Tachykinines are a family of three peptides at least, known as substance P (SP), Neurokinin A (NKA) and Neurokinin B (NKB).

Research in the field of tachykinin antagonists, initially directed toward single or multiple replacement of amino acids of the peptide agonists sequence of Substance P and of the other tachykinins, brought to the discovery of nonapeptides containing one or more D-tryptophan units [Regoli et al., Pharmacol., 28, 301 (1984)].

On the other hand, the problems related to the use of high-molecular-weight peptides as drugs (multiplicity of enzymatic hydrolytic attack sites, poor bioavailability, rapid excretion from the liver and kidneys) spurred to search for the minimum peptide fragment still capable of exerting an antagonist action. These studies brought to the singling out of suitably derivatized SP antagonists tripeptides and dipeptides European patents Nos. 333174 and 394989). Recently it has been reported a new class of tachykinin receptor antagonists, not containing natural AMINO ACIDS, and

DETAILED DESCRIPTION OF THE INVENTION

It has surprisingly been found—and this finding constitutes a fundamental feature of the present invention—that non-peptidic compounds of general formula (I) as defined above are good inhibitors of the tachykinins bond to NK1 receptor and have a sufficient metabolic stability.

A preferred group of compounds under the present invention includes compounds of formula (I) wherein:

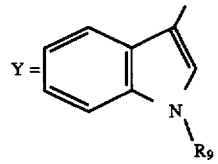

and Z=CO, R8=H, X=NR7COR6 and R1, R2, R3, R4, R5, R6, R7, R9, R10, R11, A, and B are as defined above.

Particularly preferred products are compounds of general formula (I) wherein:

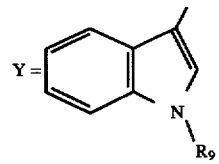

and Z=CO, R8 =H, R5=2-methylnaphthyl X=NR7COR6, R6=benzyl, R7=tethyl and the other substituents are as defined above.

The present description sets forth the following substituent groups as particularly preferred: the alkyl radical is selected out of a group consisting of methyl, ethyl, propyl, butyl, and pentyl; halogen, as used herein, means fluoro, chloro, bromo and iodo.

In view of the asymmetry centres of formula (I), this invention refers to the various diastereoisomers of said formula; in particular, substituent R5 is preferably in S-position and the amino and carboxy groups on the cyclohexane unit can assume the (1R,2S) and (1S,2R) configuration. The compounds under the present invention proved to be SP, Neurokinin A, and Neurokinin B receptor antagonists. Therefore, they can be utilised for the prevention and treatment of diseases where tachykinins (SP, NKA, NKB) play a neuromodulating role, such as respiratory conditions (e.g. asthma, allergic rhinitis) [Peters et al Amer.Rev.Resp.Dis.145.A 835 (1992)], ophthalmic conditions (e.g. conjunctivitis) , cutaneous conditions (e.g. allergic dermatitis, dermatitis by contact, psoriasis) [Hamelet et al, Can J. Pharm. Physiol. 66,1361 (1988)], intestinal conditions (e.g. ulcerative colitis, Crohn's disease)[Mantyh et al, Proc.Natl. Acad.Sci.U.S.A.85,3235 (1988)].

The present invention referred to pharmaceutical compositions containing as active ingredient a compound of general formula (I) in admixture with an organic or inorganic pharmaceutically acceptable carrier. The suitable carriers include substances usually employed in manufacturing preparation as inert diluents, lubricants, dispersing and surface active agents, aqueous, oil or glycolic suspensions. Such compositions, prepared following known procedures, consisted pills, tablets, pellets, solutions, suspension emulsion, suppositories, and may be administered orally, topically, rectally parenterally and as retard form.

An appropriate dosage level will generally be about 0.04 to 40 mg per Kg patient body weight per day and may be administered on a regimen of 1 to 3 times per day.

Another fundamental object of the invention is the preparation of compounds of general formula (I) by condensation.

Compounds of general formula (I) as defined are prepared condensing, in the presence of a suitable condensing agent, intermediate of formula (II)

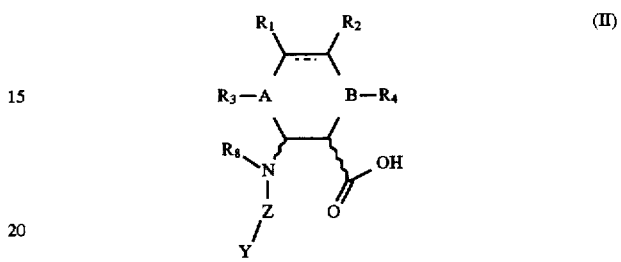

with intermediate of formula (III)

where R1, R2, R3, R4, R5, R8, Y, Z, X, A and B are as defined above, said compound of formula (II), wherein Z=CH2, R8=H, being prepared following the synthetic scheme (1) below reported.

Scheme 1

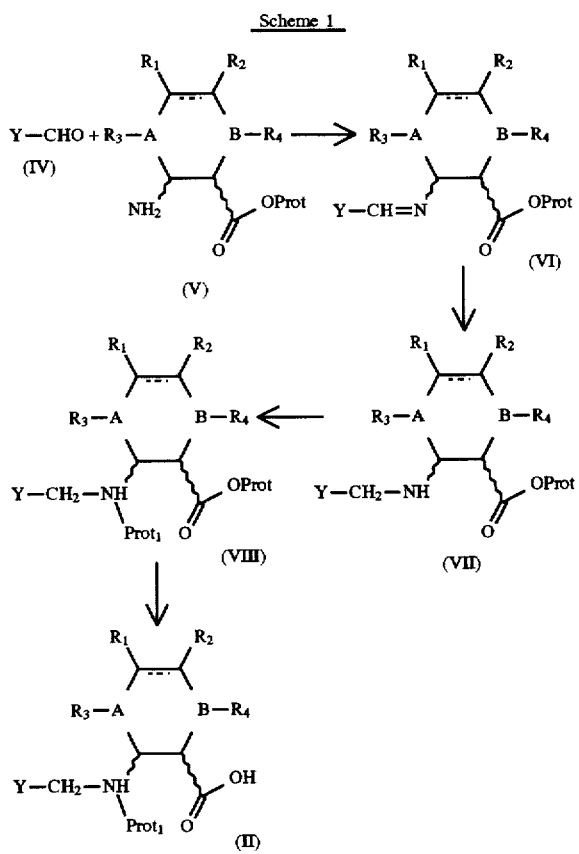

The synthetic scheme 2

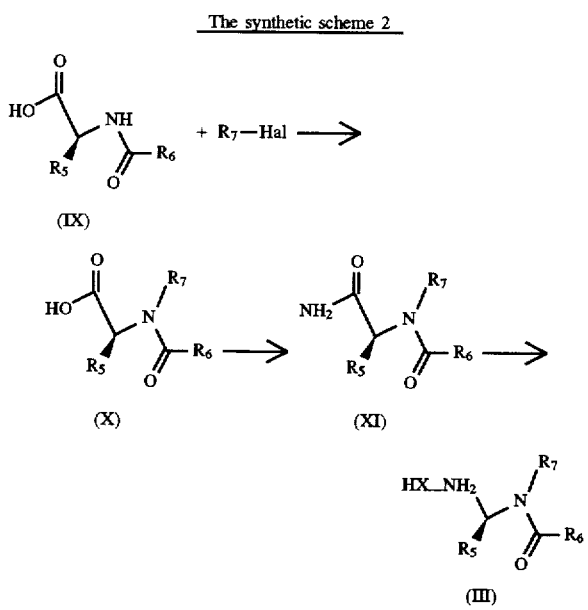

illustrates the preparation of an intermediate of formula (III), where X=NR7COR6 and the configuration of the carbon atom linked to R5 is preferably S, said compound being prepared by reaction between the D-aminoacid derivative of formula (IX), commercially available or synthesised as described in the examples or through synthetic routes obvious for those skilled in the art, and the requisite alkyl halide of general formula R7-Hal, wherein Hal is selected from the group consisting of chloro, iodo and bromo and R7 is as defined above, in presence of a active hydride reagents in aprotic polar solvent as dioxane or tetrahydrofuran. Preferably the reaction is carried out at 0° C. in tetrahydrofuran employing as a base sodium hydride and as alkylating agent methyl iodide. The following reaction with N- hydroxybenzotriazole ammonium salt in presence of a suitable condensing agent, produces the corresponding amide and, by treatment with bis(trifluoroacetoxy)iodobenzene, to the gem-diamine derivate (III). The crude product is purified by chromatography or crystallisation.

Excellent product yield and purity were obtained using benzotriazolyloxy tripyrrolidine phosphonium hexafluorophosphate (PyBOP) as a condensing agent. In particular, the reaction was carried out by addition of slight excess of PyBOP to a carboxylic component (formula II) solution, maintained at low temperature, followed by addition of the aminic component hydrochloride (formula VI) and a quantity of tertiary amine of three equivalents in respect of the condensing agent.

An alternative procedure envisages the use, as a condensing agent, of 1-ethyl-3-(3'-dimethylaminopropyl)-carbodiimide (WSC. HCl).

The compounds of this invention can exist in different isomeric configurations. In fact, the configuration of the carbon atom bound to substituent R5 is univocally determined by the synthesis starting compound being of formula VI. However, the other starting compound (i.e. 2-aminocyclohexanecarboxylic acid as per formula II) has 2 asymmetric carbon atoms and usually consists of an inseparable mixture of two enantiomers, whose ring substituents are cis. It follows that the compounds of this invention are mixtures of diastereoisomers. Said mixtures can be easily resolved by chromatography. In any case, compounds of formula (I) can be used both in optically active form and in the form of isomeric mixtures.

The following examples illustrate some embodiments of the claimed invention and the synthesis procedure thereof.

EXAMPLE 1 benzyl ester of $N^{\alpha}$-{[N(1(H)indol-3-yl-carbonyl)(1R,2S)-2-aminocyclohexan carbonyl}-L-phenylalanine and benzyl ester of $N^{\alpha}$-{[1(H)N(indol-3-yl-carbonyl) (1S,2R)-2-aminocyclohexancarbonyl}-L-phenylalanine 1a) WSC.HCl (89 mg, 0.46 mmol) was added to a chilled solution of cis N-(1(H)indol-3-yl-carbonyl)-2-aminocyclohexancarboxylic acid (prepared as described in WO-94/013694) (111 mg, 0.388 mmol) and N-hydroxybenzotriazole (HOBt) (76 mg, 0.50 mmol) in CH2Cl2 (1 ml)/dimethylformamide (DMF) (0.5 ml). The solution was stirred at 0° C. for 20 min., then hydrochloride of L-phenylalanine benzyl ester (150 mg, 0.514 mmol) was added, followed by dropwise addition of diisopropylethylamine (to pH 9). The resulting solution was stirred at 0° C. for 30 min. then at room temp. for 72 h. The CH2Cl2 was removed in vacuo, the residue treated with H2O (30 ml), and the emulsion extracted with diethyl ether (1×200 ml). The layers were separated, and the organic phase washed with 1N HCl (2×50 ml), H2O, 5% NaHCO3 (2×50 ml), H2O and brine, then dried (Na2SO4), filtered and the filtrate concentrated in vacuo. The two diastereoisomers were separated by reversed-phase on a 7 μ Lichrosorb R RP-18 column (Hibar Merck R) eluting with:

A=0.1% trifluoroacetic acid in acetonitrile;

B=0.1% trifluoroacetic acid in water; gradient of 45% to 25% of A over 2 h; flow rate 9 ml/min; effluent monitored at 230 nm (UV detector).

The fractions corresponding to the two peaks of the two isolated diastereoisomers were joined, concentrated to small volume at a reduced pressure and repeatedly freeze-dried, giving 59 mg, (30% yield) and 64.2 mg, (32% yield) of the two diastereoisomers.

HPLC analysis on a Phase Separation Spherisorb ODS-2 5 46×250 mm column under isocratic conditions at 35% of A. flow 1 ml/min, showed a single peak for each of the two products (denominated "fast" and "slow" depending on their being eluted at an earlier or, respectively, at a later time):

HPLC (fast)=9.34 min HPLC (slow)=10.02 min

EXAMPLE 2

1-{N-(1(H)indol-3-yl-carbonyl) (1R,2S)-2-aminocyclohexanecarbonyl}-amino-1-(phenylacetyl) amino-2-phenyl-ethane and 1-{N-(1(H)indol-3-yl-carbonyl) (1S,2R)-2-aminocyclohexanecarbonyl}-amino-1-(phenylacetyl)amino-2-phenyl-ethane 2a) Dicyclohexylcarbodiimide (348 mg, 1.69 mmol) was added to a chilled solution of Boc-L-phenylalanine (387 mg, 1.46 mmol) and the ammonium salt of 1-hydroxybenzotriazole (248 mg, 1.63 mmol) in DMF (5 ml). The solution was stirred at 0° C. for 90 min, then at room temperature for 2 h. The reaction mixture was filtered, and the filtrate poured into water (77 ml). The emulsion was extracted with diethylether (1×200 ml), the layers separated, and the organic phase washed with 5% NaHCO3, water and brine, then dried (sodium sulphate), filtered, and the filtrate concentrated in vacuo to give Boc-L-phenylalanine amide (370 mg, 96%). Analytical HPLC in the condition of example 1a), using a linear gradient of 20% A to 80% A over 25 min, then 80% A for 10 min, showed a single peak at 14.92 min.

2b) the amide obtained under 2a) above (261 mg, 0.988 mmol) was added to a trifluoroacetic acid (TFA)/water solution (1:1, 6 ml). This solution was stirred at room temperature for 15 min, then the solvents were removed in vacuo. The residue was azeotroped with hexane (2×10 ml), then recrystallised from ethyl acetate-hexane to give L-phenylalanine amide as it's TFA salt (202 mg, 73%). Analytical HPLC in the condition of example 2a),showed a single peak at 3.29 min.

2c) Diisopropylethylamine (233 ml, 1.34 mmol) was added at room temperature to a solution of the amide obtained under 2b) above (124 mg, 0.446 mmol), 2-methyl-2-(o-nitrophenoxy) propionic acid (103 mg, 0.457 mmol) and PyBOP (234 mg, 0.450 mmol) in DMF (2 ml). After 1 h the solution was poured into water (15 ml) and the emulsion extracted with diethyl ether (30). The organic phase was washed with 5% NaHCO3, water, 0.1N HCl, and brine, then dried (Na2SO4), filtered and the filtrate concentrated in vacuo. The crude product was purified by column chromatography [SiO2: 5% MeOH/CHCl3] to give the amide of N-(2-methyl-2(o-nitrophenoxy)propanoyl)L-phenylalanine (129 mg, 78%). Analytical HPLC in the condition of example 2a), showed a single peak TR=17.74 min; TLC (5% MeOH/CHCl3) rf=0.23.

2d) Bis (trifluoroacetoxy)iodobenzene (50 mg, 0.12 mmol) was dissolved in acetonitrile (4 ml), water (4 ml) was added followed by the amide obtained under 2c) above (43 mg, 0.12 mmol). After 3 h at room temp.

Analytical HPLC in the condition of example 2a) showed no starting material remained. The acetonitrile was removed in vacuo, and the residue treated with 4N HCl (30 ml, 0.12 mmol). The solution was concentrated in vacuo, and the residue triturated with ether to give hydrochloride of 1-(2-methyl-2(o-nitrophenoxy)propanoyl)amino-1-amino-2-phenylethane (42 mg, 91%) as a hygroscopic solid. Analytical HPLC in the condition of example 2a), showed a single peak TR=17.32 min. No further purification was attempted.

2e) Diisopropylethylamine (239 ml, 1.37 mmol) was added to a mixture of phenylacetic acid (66 mg, 0.48 mmol), PyBOP (240 mg, 0.461 mmol), and the amine obtained under 2d) above (174 mg, 0.458 mmol) in tetrahydrofuran (THF) (3 ml). The resulting yellow solution was stirred at room temp. for 7 h. The THF was removed in vacuo, and the residue dissolved in ethyl acetate (100 ml). This solution was washed with 5% NaHCO3 (25 ml), H2O, 1N HCl (3'25 ml) and brine, then dried (Na2SO4), filtered and the filtrate concentrated in vacuo. The crude product was purified by column chromatography [SiO2: ethyl acetate-hexane 1:1] to give 1-(2-methyl-2(o-nitrophenoxy) propanoyl) amino-1-(phenylacetyl) amino-2-phenylethane (112 mg, 53%). Analytical HPLC in the condition of example 2a), showed a single peak TR=23.50 min; TLC (5% MeOH/CHCl3) rf=0.66.

2f) Hydrogen gas was bubbled through a mixture of diamide obtained under 2e) above (110 mg, 0.238 mmol) and 10% Pd/carbon (11 mg) in acetic acid (2 ml), for 2 ½ h. The mixture was filtered through Celit®, the filter aid was washed with acetic acid (3×3 ml), and the combined filtrate concentrated in vacuo. The residue was washed with cyclohexane (5×4 ml), the solid filtered and dried in vacuo, to give acetate of 1-amino-1-(phenylacetyl) amino-2-phenylethane (72 mg, 96%). Analytical HPLC in the condition of example 2a), showed a single peak TR=16.92 min (broad). 2g) WSC.HCl (55 mg, 0.29 mmol) was added to a chilled solution of cis N-(1(H)indol-3-yl-carbonyl)-2-aminocyclohexancarboxylic acid (61 mg, 0.21 mmol) and HOBt (45 mg, 0.29 mmol) in THF (2 ml). The resulting solution was stirred at 0° C. for 30 min, then a solution of acetate of 1-amino-1-(phenylacetyl) amino-2-phenylethane obtained under 2f) above (74 mg, 0.23 mmol) in THF (1 ml) was added, followed by dropwise addition of diisopropyl-ethylamine (until pH 9). This solution was stirred at 0° C. for 30 min, then at room temp. for 18 h. The solvent was removed in vacuo and the residue dissolved in ethyl acetate (100 ml). The solution was washed with 1N HCl (2×25 ml), water, 5% NaHCO3 (2×25 ml), water and brine, dried (Na2SO4), filtered and the filtrate concentrated in vacuo. The crude product was purified by preparative RP-HPLC, eluting with a gradient of 44% A to 64% A over 2 h, to give the two diastereoisomers fast (12 mg, 11%) and slow (28 mg, 25%). HPLC analysis in the condition of example 2a), showed a single peak for each of the two products (denominated "fast" and "slow" depending on their being eluted at an earlier or, respectively, at a later time):

HPLC (fast)=22.48 min HPLC (slow)=23.04 min

EXAMPLE 3

1-{N-(1(H)indol-3-yl-carbonyl) (1R,2S)-2-aminocyclohexanecarbonyl}-amino-1-(N-methyl-N-phenylacetyl)amino-2(2-naphthyl)ethane and 1-{N-(1(H)indol-3-yl-carbonyl)(1S,2R)-2-aminocyclohexanecarbonyl}-amino-1-(N-methyl-N-phenylacetyl) amino-2(2-naphthyl)ethane 3a) Bis(trimethylsilyl)acetamide (1.84 ml, 7.46 mmol) was added, at room temp., to a suspension of D-3-(2-naphthyl)alanine (801 mg, 3.73 mmol) in THF (8 ml). The mixture was stirred at room temp. until complete solution occurred (ca. 2 h), then cooled to 0° C., and a solution of phenylacetic acid chloride (571 mg, 3.68 mmol) in THF (4 ml) added. The resulting solution was stirred at 0° C. for 30 min. then at room temperature for 18 h.

Water (30 ml) was added, the mixture stirred for 20 min, then filtered. The solid was washed with H2O and ethyl acetate, and the combined filtrate concentrated in vacuo to remove the organic solvents (a precipitate appeared). This solid was filtered, and air-dried to give N-(Phenylacetyl)-D-naphthyl)alanine (1.19 g, 96%); TLC (20% acetic acid/toluene) rf=0.19; Analytical HPLC in the condition of example 2a), showed a single peak TR=21.56 min; [a]D=−27.7° (c=0.87, DMF).

3b) Sodium hydride (112 mg of an 80% dispersion in mineral oil), was added to a chilled solution of the product obtained under 3a) above (405 mg, 1.22 mmol) and methyl iodide (605 ml, 9.72 mmol) in THF (4 ml). The mixture was stirred at 0° C. for 30 min., then at room temp. for 22 h. The reaction was quenched by adding ethyl acetate (40 ml) and H2O (10 ml). The layers were separated, and the organic phase extracted with 5% NaHCO3 (20 ml). The combined aqueous extracts were cooled, acidified to pH 2 with 4N HCl, and extracted with ethyl acetate (100 ml). The organic phase was washed with 5% Na2S2O3, H2O and brine, then dried (Na2SO4), filtered and the filtrate concentrated in vacuo. The crude product was purified by preparative RP-HPLC, using a gradient system of 64% (H2O+0.1% TFA): 46% (CH3CN+0.1% TFA) to 44% A: 56% B over 2 h, to give N-methyl-N-phenylacetyl-D-naphthylalanine (279 mg, 66%); TLC (20% acetic acid/toluene) rf=0.29. Analytical HPLC in the condition of example 2a), isocratic elution with 52% A, showed a single peak TR=10.31 min; [a]D=+49.8° (c=1.01, DMF)

3c) WSC.HCl (104.5 mg, 0.544 mmol) was added to a chilled solution of acid 3b (157.6 mg, 0.454 mmol) and the ammonium salt of HOBt (82.6 mg, 0.543 mmol) in DMF (2 ml). The solution was stirred at 0° C. for 50 min, then at room temp. for 30 min. H2O (20 ml) was added and the emulsion extracted with diethyl ether (200 ml). The organic phase was washed with 5% NaHCO3 (2×50 ml), H2O, 1N HCl (2×50 ml), H2O and brine, dried (Na2SO4), filtered, and the filtrate concentrated in vacuo. The crude product was purified by column chromatography [SiO2: 8% MeOH/CHCl3] to gave N-methyl-N-phenylacetyl-D-naphthylalanine amide, (147 mg, 94%); TLC (10% MeOH/CHCl3) rf=0.39. Analytical HPLC in the condition of example 2a), isocratic elution with 52% A, showed a single peak TR=9.63 min; [a]D=+110° (c=0.91, CHCl3).

3d) Bis (260 mg, 0.606 mmol) was dissolved in CH3CN (1.5 ml), H2O (1.5 ml) was added, followed by amide 3c (133.4 mg, 0.386 mmol). The solution was stirred at room temp. for 20 min, then diluted with H2O (9 ml) and acidified with 1N HCl (9 ml). The emulsion was extracted with diethyl ether (30 ml), the layers separated, and the aqueous phase freeze-dried to give hydrochloride of 1-amino-1-(N-methyl-N-phenylacetyl) amino-2(2-naphthyl)ethane (93 mg, 68%), which was used the following step without isolation.

3e) WSC.HCl (59.1 mg, 0.308 mmol) was added to a chilled solution of cis N-(1(H)indol-3-yl-carbonyl)-2-aminocyclohexancarboxylic acid (73.3 mg, 0.256 mmol) and HOBt (53.9 mg, 0.352 mmol) in CH2Cl2 (2 ml)/DMF (0.5 ml). The solution was stirred at 0° C. for 30 min., amine hydrochloride 3d (89 mg, 0.25 mmol) in CH2Cl2 (1 ml)/DMF (1 ml) was added, followed by dropwise addition of diisopropylethylamine (to pH 9). The reaction was stirred at 0° C. for 30 min., then at room temp. for 18 h. The CH2Cl2 was removed in vacuo, H2O (10 ml) added, and the emulsion extracted with diethyl ether (100 ml). The layers were separated and the organic phase washed with 1N HCl (2×25 ml), H2O, 5% NaHCO3 (2×25 ml), H2O and brine, then dried (Na2SO4), filtered, and the filtrate concentrated in vacuo. The crude product was purified by preparative RP-HPLC in the condition of example 1a), eluting with a gradient of 55% A to 75%. A over a period of 2 h, to give diastereoisomer fast (44.1 mg, 30%); [HPLC (isocratic 65% A) TR=9.36 min], and diastereoisomer slow (36.7 mg, 25%); [HPLC (isocratic 65% A) TR=11.34 min).

EXAMPLE 4

S-2-N (1(H)indol-3-yl-carbonyl)-(1R,2S)cis-2-aminocyclohexan-carboxamide)-1(3,5-bis(trifluoromethyl) phenyl)methyloxy)-3(2-naphthyl)propane and S-2-N(1(H) indol-3-yl-carbonyl)-(1S,2R)cis-2-aminocyclohexan-carboxamide)-1(3,5-bis(trifluoromethyl)phenyl) methyloxy) -3(2-naphthyl)propane 4a) Lithium aluminium hydride in THF [1.0M] (6.1 ml, 6.1 mmol) was added dropwise to a chilled suspension of L-naphthylalanine (657 mg, 3.05 mmol) in THF (3 ml). When the addition was complete the cooling bath was removed and the mixture warmed to room temp. (vigorous gas evolution), then for 1 h. after which time TLC (Chloroform/methanol/acetic acid 85/10/5 V/V)) showed none of the amino acid remained. The mixture was cooled to room temp. and quenched by cautiously adding H2O (0.34 ml), followed by 15% NaOH (0.34 ml) and H2O (1 ml). The resulting mixture was stirred at room temp. for 30 min., filtered, and the filtrate concentrated in vacuo. The residue was partitioned between ethyl acetate (50 ml) and 1N HCl (100 ml), the layers were separated, and the aqueous phase basified to pH 10 with 10N NaOH. The aqueous phase was extracted with ethyl acetate (2×100 ml), the layers separated, and the organic phase washed with brine, dried (Na2SO4), filtered, and the filtrate concentrated in vacuo to give amino alcohol (S)-2amino-3(2naphthyl)propan-1-ol (443 mg, 72%); TLC (10% MeOH/CHCl3) rf=0.12.

4b) Ditertbutyldicarbonate (127 mg, 0.582 mmol) was added to a solution of amino alcohol 4a) (105 mg, 0.520 mmol) in CH2Cl2 (2 ml). The mixture was stirred at room temperature for 18 h, then the solvent was removed in vacuo, and the residue purified by column chromatography [SiO2: ethyl acetate-hexane 1:1] to give the (S)-2-(1,1-dimethylethyloxycarbonyl)amino-3(2-naphthyl)propan-1-ol (112 mg, 71%); TLC (ethyl acetate-hexane 1:1) rf=0.35.

4c) Triphenylphosphine (371 mg, 1.41 mmol) was added to a solution of 3,5-bistrifluoromethylbenzyl alcohol (257 mg, 1.05 mmol) in dry CCl4 (2 ml). The mixture was refluxed for 1 h, then cooled to room temp. Pentane (2 ml) was added, and the mixture stirred for a further 5 min., then filtered. The solid was washed with pentane (2 ml), and the filtrate concentrated in vacuo. The crude product was purified by column chromatography [SiO2: hexane-ethyl acetate 4:1] to give 3,5-bistrifluoromethylbenzyl chloride (162 mg, 59%); TLC (hexane-ethyl acetate 1:1) rf=0.73.

4d) Sodium hydride (15 mg of an 80% dispersion in mineral oil) was added to a solution of the product obtained under 4b) above (110.3 mg, 0.366 mmol) in DMF (1 ml) at −10° C. The mixture was stirred at −10° C. for 10 min., chloride 4c) (147 mg, 0.560 mmol) in DMF (1 ml) was added, and the stirring continued at −10° C. for 15 min, then at room temp. for 4 h. Saturated NH4Cl (2 ml) was added, the solution diluted with H2O (20 ml), and extracted with ethyl acetate (2×50 ml). The organic extract was dried (Na2SO4), filtered, and the filtrate concentrated in vacuo. The crude product was purified by column chromatography [SiO2: hexane-ethyl acetate 3:1] to give (S)-2-(1,1-dimethyl-ethyloxycarbonyl)amino-1-((3,5-bis(trifluoromethyl)methoxy)-3(2-naphthyl)propane (135 mg, 70%); TLC (hexane-ethyl acetate 2:1) rf=0.66

4e) A saturated solution of HCl in ethyl acetate (2 ml) was added dropwise to a chilled solution of ether 4d) (118 mg, 0.224 mmol) in CH2Cl2 (2 ml). The cooling bath was removed and the solution stirred at room temp. for 1 h (a precipitate appeared). The excess HCl was removed by bubbling N2 through the mixture, the solid was filtered, washed with hexane, and air-dried to give (S)-2-amino-1-( (3,5-bis(trifluoromethyl)methoxy)-3(2-naphthyl)propane hydrochloride (85.7 mg, 82%); TLC (CMA) rf=0.36

4f) WSC.HCl (42.6 mg, 0.222 mmol) was added to a chilled solution of acid cis N-(1(H)indol-3-yl-carbonyl)-2-aminocyclohexancarboxylic acid (53.5 mg, 0.187 mmol) and HOBt (32.3 mg, 0.211 mmol) in CH2Cl2(1 ml)/DMF (0.25 ml). The solution was stirred at 0° C. for 25 min., the product obtained under 4b) above (81.9 mg, 0.177 mmol) was added, followed by dropwise addition of diisopropylethylamine (to pH 9). Stirring was continued at 0° C. for 30 min, then at room temp. for 18 h. The CH2Cl2 was removed in vacuo, H2O (10 ml) was added, and the emulsion extracted with diethyl ether (50 ml). The layers were separated, the organic phase was washed with 1N HCl (2×25 ml), H2O, 5% NaHCO3 (2×25 ml), H2O, and brine, dried (Na2SO4), filtered, and the filtrate concentrated in vacuo. The crude product was purified by preparative RP-HPLC, eluting with a gradient of 25% A (H2O+0.1% TFA): 75% B (methanol) to 5% A: 95% B over a period of 2 h, to give diastereoisomer fast (50.6 mg, 41%); HPLC (isocratic 88% B) TR=8.40 min., and diastereoisomer slow (50.3 mg, 41%); HPLC (isocratic 88% B) TR=9.46 min.

Following the procedures described in Examples 1–4, these compounds were also obtained:

5) 1-{N-(1(H) indol-3-yl-carbonyl) (1R,2S)-2-aminocyclohexanecarbonyl}-amino-1-N(phenylacetyl) amino-2(2-naphthyl)ethane and 1-{N-(1(H)indol-3-yl-carbonyl) (1S,2R)-2-aminocyclohexanecarbonyl}-amino-1-N(phenylacetyl) amino-2(2-naphthyl)ethane HPLC: column Phase Sep. Spherisorb ODS-2 5 mm (250×4.6) fitted with a Phase Sep. Spherisorb S5 ODS-2 (50×4.6 mm) precolumn; eluent A: H2O, 0.1% trifluoroacetic acid; eluent B:

Acetonitrile, 0.1% trifluoroacetic acid; UV Detection 215 nm; flow 1 ml/min; linear gradient from 20% to 80% B in 20 min, then isocratic 80% B for 10 min (HPLC System 1):

fast: TR=24.55 min slow TR=25.07 min;

TLC(SiO2)CHCl3/CH3OH (9:1 v/v) Rf=0.37 and 0.40

6) 1-{N-(1(H)indol-3-yl-carbonyl)(1R,2S)-2-aminocyclohexanecarbonyl}-amino-1- (N-methyl-N-phenylacetyl) amino-2-phenylethane and 1-{N-(1(H)indol-3-yl-carbonyl) (1S,2R)-2-aminocyclohexanecarbonyl}-amino-1-(N-methyl-N-phenylacetyl) amino-2-phenylethane HPLC: (System 1)

fast: TR=23.4 min slow TR=24.5 min;

TLC(SiO2)CHCl3/CH3OH (90:10 v/v) Rf=0.67 and 0.84

7) 1-{N-(1(H)indol-3-yl-carbonyl)(1R,2S)-2-anminocyclohexanecarbonyl}-amino-1-(N-methyl-N((2-naphthyl)acetyl))a mino-2-phenylethane and 1-{N-(1(H)indol-3-yl-carbonyl) (1S,2-R)-2-aminocyclohexanecarbonyl}-amino-1-(N-methyl-N((2-naphthyl)acetyl)) amino-2-phenylethane HPLC: column Phase Sep. Spherisorb ODS-2 5 mm (250×4.6 mm) fitted with a Phase Sep. Spherisorb S5 ODS-2 (50×4.6 mm) precolumn; eluent A: H2O, 0.1% trifluoroacetic acid; eluent B:

Acetonitrile, 0.1% trifluoroacetic acid; UV Detection 215 nm; flow 1 ml/min; (HPLC system 2) isocratic 70% B;

fast: TR=4.83 min slow TR=5.74 min;

8) 1-{N-(1(H)indol-3-yl-methyl)(1R,2S)-2-aminocyclohexanecarbonyl}-amino-1-N(phenylacetyl) amino-2(2-naphthyl) ethane and 1-{N-(1(H)indol-3-yl-methyl) (1S, 2R) -2-anminocyclohexanecarbonyl}-amino-1-N(phenylacetyl) amino-2 (2-naphthyl) ethane HPLC: (System 1) fast: TR=21.36 min slow TR=22.42 min; TLC(SiO2) CHCl3/CH3OH (95:5 v/v) Rf=0.15 and 0.17

9) 1-{N-(1(H)indol-3-yl-carbonyl)(1R,2S)-2-aminocyclohexanecarbonyl}-amino-1-(N-methyl-N-((S)2-phenylpropionyl))amino-2-(2-naphthyl)ethane and 1-{N-(1(H)indol-3-yl-carbonyl) (1S,2R)-2-aminocyclohexanecarbonyl}-amino-1-(N-methyl-N-((S)2-phenylpropionyl)) amino-2-(2-naphthyl)ethane HPLC:(System 1) fast: TR=27.04 min slow TR=27.42 min;

TLC(SiO2) CHCl3/CH3OH (95:5 v/v) Rf=0.26 and 0.26

10) 1-{N-(1(H)indol-3-yl-carbonyl)(1R,2S)-2-aminocyclohexane-carbonyl}-amino-1-(N-methyl-N-((R)2-phenylpropionyl))Ammino-2-(2-naphthyl)ethane and 1-{N-(1(H)indol-3-yl-carbonyl) (1S,2R)-2-aminocyclohexanecarbonyl}-amino-1-(N-methyl-N-((R)2-phenylpropionyl)) amino-2- (2-naphthyl) ethane HPLC: (System 2) isocratic 65% B fast: TR=12.14 min slow TR=16.5 min;

11) 1-{N-(1(H)indol-3-yl-carbonyl)(1R,2S)-2-aminocyclohexanecarbonyl}-amino-1-(N-methyl-N-4-chlorophenylacetyl)amino-2(2-naphthyl)ethane and 1-{N-(1(H)indol-3-yl-carbonyl)(1S,2R)-2-aminocyclohexanecarbonyl}-amino-1-(N-methyl-N-4-chlorophenylacetyl) amino-2(2-naphthyl)ethane HPLC: (System 1)

fast: TR=27.7 min slow TR=28.8 min;

12) 1-{N-(1(H)indol-3-yl-carbonyl)(1R,2S)-2-aminocyclohexanecarbonyl}-amino-1-(N-methyl-N-4-methylphenylacetyl)amino-2(2-naphthyl)ethane and 1-{N-(1(H)indol-3-yl-carbonyl)(1S,2R)-2-aminocyclohexanecarbonyl}-amino-1-(N-methyl-N-4-methylphenylacetyl) amino-2(2-naphthyl)ethane HPLC: (System 1)

fast: TR=27.7 min slow TR=28.94 min;

13) 1-N-[N(benzoyl)-(R,S)cis-2-amino-ciclohexane-carbonyl]-amino-1-[N(methyl)N(phenylacetyl)]amino-2(2-naphthyl)ethane and 1-N-[N(benzoyl)-(S,R) cis-2-amino-ciclohexane-carbonyl]-amino-1-[N(ethyl)N(phenylacetyl)] amino-2(2-naphthyl)ethane 14) 1-N-[N(4-methyl-benzoyl)-(R,S)cis-2-amino-ciclohexane-carbonyl]-amino-1-[N(methyl)N (phenylacetil)] amino-2(2-naphthyl)ethane and 1-N-[N(4-methyl-benzoil)-(S,R)cis-2-amino-cyclohexane-carbonyl] amino-1-[N(methyl)N(phenylacetil)]amino-2(2-naphthyl) ethane 15) 1-N-[N(4-metossi-benzoil)-(R,S)cis-2-amino-cyclohexane-carbonyl]-amino-1-[N(methyl)N(phenylacetil) ]amino-2(2-naphthyl)ethane and 1-N-[N(4-metossi-benzoil)-(S,R)cis-2-amino-cyclohexane-carbonyl]amino-1-[N(methyl)N(phenylacetil)]-amino-2(2-naphthyl)ethane 16) 1-N-[N(4-cloro-benzoil)-(R,S)cis-2-amino-cyclohexane-carbonyl]-amino-1-[N(methyl)N(phenylacetil)]amino-2(2-naphthyl)ethane and 1-N-[N(4-cloro-benzoil)-(S,R)cis-2-amino-cyclohexane-carbonyl]amino-1-[N(methyl)N(phenylacetil)]amino-2 (2-naphthyl)ethane 17) 1-N-[N(3,4-cloro-benzoil)-(R,S)cis-2-amino-cyclohexane-carbonyl]-amino-1-[N(methyl)N (phenylacetil) ] amino-2(2-naphthyl) ethane and 1-N-[N(3,4-cloro-benzoil)-(S,R)cis-2-amino-cyclohexane-carbonyl] amino-1-[N(methyl)N(phenylacetil)]amino-2(2-naphthyl) ethane 18) 1-N-[N( 1(Methyl)indol-3-yl-carbonyl)-(R,S) cis-2-amino-cyclohexane-carbonyl]-amino-1-(N(methyl)N (phenylacetil)]amino-2(2-naphthyl)ethane and 1-N[N(1 (methyl)indol-3-yl-carbonyl)-(S,R) cis-2-amino-cyclohexane-carbonyl]amino-1-[N(methyl) N(phenylacetil)] amino-2(2-naphthyl) ethane 19) 1-N-[N(1(methyl)indol-3-yl-carbonyl)-N-methyl-(R, S)cis-2-amino-cyclohexane-carbonyl]-amino-1-[N(methyl) N(phenylacetil)]amino-2 (2-naphthyl)ethane and 1-N-[N(1 (methyl)indol-3-yl-carbonyl)-N-methyl-(S,R)cis-2-amino-cyclohexane-carbonyl]amino-1-[N(methyl)N(phenylacetil)] amino-2-(2-naphthyl)ethane 20) 1-N-[N(1(H)indol-3-yl-carbonyl)-(R,S)cis-2-amino-cyclohexane-carbonyl]-amino-1-[N(methyl)N (phenylacetil)] amino-2(p-metossi)phenylethane and 1-N-[N(1(H)indol-3-yl-carbonyl)-(S,R)cis-2-amino-cyclohexane-carbonyl]amino-1-[N(methyl)N(phenylacetil)] amino-2(p-metossi)phenylethane 21) N-[N(1(Methyl)indol-3-yl-carbonyl)-N-methyl-(R,S) cis-2-amino-cyclohexane-carbonyl]-2-naphthylalanine N-methyl-N-benzilamide and N[N(1(methyl)indol-3-yl-carbonyl)-N-methyl-(S,R)cis-2-amino-cyclohexane-carbonyl]-2-naphthylalanine-N-methyl-N-benzilamide.

Assessment of biological activity (antagonist activity on NK1 receptor) of compounds of this invention was performed by means of the following binding and functional assays:

[3H] SP binding assay in IM9 Cell Line

Binding assay was performed with intact cells as described by Goso et al (Eur.J.Pharmacol. 254,221,1994).

Measurement of pA2 in isolated guinea pig ileum

Male albino guinea-pigs weighing 300–350 g were stunned and bled. A segment of ileum was excised and placed in oxygenated Krebs solution containing 10 mM indomethacin. After 90 min. equilibration period a cumulative concentration-response curve for the agonist, [Sar9] substance P sulfone was made. After two or more reproducible control curves for the agonist had been obtained, the compound to be tested was added to the bath and a new curve for the agonist was determined in its presence. pA2 values were calculated by using the constrained Schild plot method. The data in Table I were obtained for compound of formula (I):

TABLE I

Substance P antagonism Results

| Compounds | pKi |
|---|---|
| 1 (fast) | <6 |
| 2 (fast) | <6 |
| 3 (fast) | 8.4 |
| 3 (slow) | <5 |
| 4 (fast) | <5 |
| 9 (fast) | <5 |
| 10 (fast) | 8.7 |
| 11 (fast) | 8.4 |
| 12 (fast) | 8.7 |

We claim:

1. Compounds having the general formula (I)

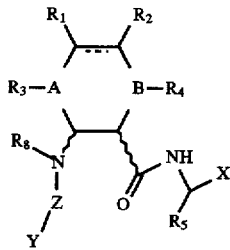

wherein:
Y is

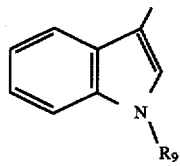

wherein $R_9$ is selected from the group consisting of H, linear or branched alkyl radicals containing 1 to 6 carbon atoms and acyl radicals $R_{10}$-CO wherein $R_{10}$ is selected from the group consisting of H, linear or branched alkyl radicals containing 1 to 3 carbon atoms;

Z is selected from the group consisting of $CH_2$ and CO;

$R_8$ is selected from the group consisting of H, linear or branched alkyl radical containing from 1 to 6 carbon atoms;

symbol ∼∼ represents a single or double bond: if the bond is single, $R_1$ and $R_2$ are selected from the group consisting of hydrogen, hydroxyl, methoxyethoxyethoxyl, methoxyethoxymethoxyl and halogen or are joined to form an epoxide, if the bond is double they are hydrogen or halogen;

A and B represent CH;

$R_3$ and $R_4$ are selected from the group consisting of hydrogen, linear or branched alkyl radicals containing from 1 to 6 carbon atoms, or are joined together to form —$(CH_2)_n$- bridge, where n stands for a whole number from 1 to 3;

$R_5$ is selected from the group consisting of: benzene, naphthyl, benzene-alkyl, naphthyl-alkyl, where the aromatic ring is unsubstituted or substituted with one or more substituents selected from the group consisting of halogen, linear or branched radicals containing from 1 to 6 carbon atoms, optionally substituted with not more than three fluorine atoms, linear or branched oxyalkyl radicals containing not more than three fluorine atoms, —$NH_2$-, $NHR_{11}$, —$N(R_{11})_2$, —$CONHR_{11}$, —$COR_{11}$, —$COOR_{11}$, —$R_{12}COOR_{11}$, —$CONHR_{11}$, —$R_{12}CONHR_{11}$, —$NHCOR_{11}$, —$NHCOOR_{11}$, —$R_{12}COOR_{11}$, nitro, wherein $R_{11}$, and $R_{12}$ are independently selected from the group consisting of H, linear or branched alkyl radicals containing from 1 to 6 carbon atoms;

X is selected from the group consisting of: —$NR_7COR_6$, —$NR_6COOR_7$, wherein $R_6$ and $R_7$ are independently selected from the group consisting of: H, alkyl, benzene, naphthyl, benzene-alkyl, naphthyl-alkyl where the aromatic ring is unsubstituted or substituted with one or more substituents selected from the group consisting of halogen, linear or branched radical containing from 1 to 6 carbon atoms, optionally substituted with not more than three fluorine atoms, linear or branched oxyalkyl radicals containing not more than three fluorine atoms, —$NH_2$-, $NHR_{11}$, —$N(R_{11})_2$, —$CONHR_{11}$, —$COR_{11}$, —$COOR_{11}$, —$R_{12}COOR_{11}$, —$CONHR_{11}$, —$R_{12}CONHR_{11}$, —$NHCOR_{11}$, —$NHCOOR_{11}$, —$R_{12}COOR_{11}$, nitro, wherein $R_{11}$, and $R_{12}$ are as above defined;

symbol ∼∼ means that the configuration of those asymmetric carbon atoms of 2-amino-cyclohexamecarboxylic acid can be either S or R with the proviso that such configuration cannot be S or R for both the asymmetric carbon atoms.

2. The compound according to claim 1 wherein Z=CO; $R_8$=H; X=$NR_7COR_6$ and $R_1$, $R_2$, $R_3$, $R_4$, $R_5$, $R_6$, $R_7$, A and B are as above defined.

3. The compound according to claim 2 wherein the alkyl radical, as indicated in all of the herein given definitions, is selected from the group consisting of methyl, ethyl, propyl, butyl and pentyl.

4. Compounds of formula (I) represented by:

1) 1-{N-(1(H)indol-3-yl-carbonyl)(1R,2S)-2-aminocyclohexane-carbonyl}-amino-1-(phenylacetyl) amino-2-phenylethane and 1-{N-(1(H)indol-3-yl-carbonyl)(1S,2R)-2-aminocyclohexane-carbonyl}-amino-1-(phenylacetyl) amino-2-phenylethane;

2) 1-{N-(1(H)indol-3-yl-carbonyl)(1R,2S)-2-aninocyclohexane-carbonyl}-amino-1-(N-methyl-N-phenylacetyl)amino-2(2-naphthyl)ethane and 1-{N-(1(H)indol-3-yl-carbonyl)(1S,2R)-2-aminocyclohexane-carbonyl}-amino-1-(N-methyl-N-phenylacetyl)amino-2(2-naphthyl)ethane;

3) 1-{N-(1(H)indol-3-yl-carbonyl)(1R,2S)-2-aminocyclo-hexanecarbonyl}-amino-1-N(phenylacetyl)amino-2(2-naphthyl)-ethane and 1-{N-(1(H)indol-3-yl-carbonyl)(1S,2R)-2-aminocyclo-hexanecarbonyl}-amino-1-N(phenylacetyl)amino-2(2-naphthyl)-ethane;

4) 1-{N-(1(H)indol-3-yl-carbonyl)(1R,2S)-2-aminocyclo-hexanecarbonyl}-amino-1-(N-methyl-N-phenylacetyl)amino-2-phenylethane and 1-{N-(1(H)indol-3-yl-carbonyl)(1S,2R)-2-aminocyclo-hexanecarbonyl}-amino-1-(N-methyl-N-phenylacetyl)amino-2-phenylethane;

5) 1-{N-(1(H)indol-3-yl-carbonyl)(1R,2S)-2-aminocyclo-hexanecarbonyl}-amino-1-(N-methyl-N((2-naphthyl)acetyl))-amino-2-phenylethane and 1-{N-(1(H)indol-3-yl-carbonyl)(1S,2R)-2-aminocyclo-hexanecarbonyl}-amino-1-(N-methyl-N((2-naphthyl)acetyl))-amino-2-phenylethane;

6) 1-{N-(1(H)indol-3-yl-methyl)(1R,2S)-2-aminocyclohexane-carbonyl}-amino-1-N(phenylacetyl)amino-2(2-naphthyl)ethane and 1-{N-(1(H)indol-3-yl-methyl)(1S,2R)-2-aminocyclohexane-carbonyl}amino-1-N(phenylacetyl)amino-2(2-naphthyl)ethane;

7) 1-{N-(1(H)indol-3-yl-carbonyl)(1R,2S)-2-aminocyclo-hexanecarbnyl}-amino-1-(N-methyl-N-((S)2-phenylpropio-nyl))-amino-2-(2-naphthyl)ethane and 1-{N-(1(H)indol-3-yl-carbonyl)(1S,2R)-2-aminocyclo-hexanecarbonyl}-amino-1-(N-methyl-N-((S)2-phenylpropionyl))-amino-2-(2-naphthyl)ethane;

8) 1-{N-(1(H)indol-3-yl-carbonyl)(1R,2S)-2-aminocyclo-hexanecarbonyl }-amino-1-(N-methyl-N-((R)2-phenylpropionyl))amino-2-(2-naphthyl)ethane and 1-{N-(1(H)indol-3-yl-carbonyl)(1S,2R)-2-aminocyclo-hexanecarbonyl}-amino-1-(N-methyl-N-((R)2-phenylpropionyl))amino-2-(2-naphthyl)ethane;

9) 1-{N-(1(H)indol-3-yl-carbonyl)(1R,2S)-2-aminocyclo-hexanecarbonyl}-amino-1-(N-methyl-N-4-chlorophenylacetyl)-amino-2-(2-naphthyl)ethane and 1-{N-(1(H)indol-3-yl-carbonyl)(1S,2R)-2-aminocyclo-hexanecarbonyl}-amino-1-(N-methyl-N-4-chlorophenylacetyl)-amino-2-(2-naphthyl)ethane;

10) 1-{N-(1(H)indol-3-yl-carbonyl)(1R,2S)-2-aminocyclo-hexanecarbonyl}-amino-1-(N-methyl-N-4-methylphenylacetyl)-amino-2-(2-naphthyl)ethane and 1-{N-(1(H)indol-3-yl-carbonyl)(1S,2R)-2-aminocyclo-hexanecarbonyl }-amino-1-(N-methyl-N-4-methylphenylacetyl)-amino-2-(2-naphthyl)ethane;

11) 1-N-[N(1(methyl)indol-3-yl-carbonyl)(R,S)cis-2-amino-cyclohexanecarbonyl]-amino-1-[N (methyl)N(phenylacetyl)]-amino-2(2-naphthyl)ethane and 1-N-[N(1(methyl)indol-3-yl-carbonyl)(S,R)cis-2-amino-cyclohexanecabonyl]-amino-1-[N(methyl)N(phenylacetyl)]-amino-2(2-naphthyl)ethane;

12) 1-N-[N(1(methyl)indol-3-yl-carbonyl)-N-methyl-(R,S)cis-2-amino-cyclohexanecarbonyl]-amino-1-[N(methyl)N(phenyl-acetyl)]-amino-2(2-naphthyl)ethane and 1-N-[N(1(methyl)indol-3-yl-carbonyl)-N-methyl-(S,R)cis-2-amino-cyclohexanecarbonyl]-amino-1-[N(methyl)N(phenyl-acetyl)]-amino-2(2-naphthyl)ethane;

13) 1-N-[N(1(H)indol-3-yl-carbonyl)(R,S)cis-2-amino-cyclohexanecarbonyl]-amino-1-[N(methyl)N(phenylacetyl)]-amino-2(p-methoxy)phenylethane and 1-N-[N(1(H)indol-3-yl-carbonyl)(S,R)cis-2-amino-cyclohexanecarbonyl]-amino-1-[N(methyl)N(phenylacetyl)]-amino-2(p-methoxy)phenylethane.

5. A pharmaceutical composition containing, as the active ingredient, an effective dose of the compound according to claim 2.

6. A pharmaceutical composition containing, as the active ingredient, an effective dose of compound according to claim 2.

7. A pharmaceutical composition containing, as the active ingredient, an effective dose of the compound according to claim 3.

* * * * *